United States Patent [19]

Woolson

[11] Patent Number: 5,007,936
[45] Date of Patent: Apr. 16, 1991

[54] SURGICAL METHOD FOR HIP JOINT REPLACEMENT

[75] Inventor: Steven T. Woolson, Los Altos, Calif.

[73] Assignee: Cemax, Inc., Fremont, Calif.

[21] Appl. No.: 157,259

[22] Filed: Feb. 18, 1988

[51] Int. Cl.⁵ .......................... A61F 2/36; A61F 2/34; A61F 2/32

[52] U.S. Cl. ...................................... 623/23; 623/22; 364/413.13

[58] Field of Search ................ 623/23, 22; 364/413.13

[56] References Cited

U.S. PATENT DOCUMENTS 3,874,003  4/1975  Moser et al. .......................... 623/23
4,704,686  11/1987  Aldinger .............................. 364/468

OTHER PUBLICATIONS

William H. Harris, "Surgical Technique Harris/Galante Porous Hip Prosthesis", 1984, pp. 9, 16, 17.
Engh et al., "Biological Fixation of the Porocoat AML Hip", 1984, pp. 12, 14, 15.
Marketing brochure by Biomet Inc., "Cement-Free Total Hip Reconstruction", 1984, pp. 1, 5, 6, 7, 8, 9.
Leo A. Whiteside, "Whiteside Total Hip System Surgical Technique," Nov. 1985, pp. 3, 5, 6, 7.
Marketing brochure by Biomet Inc., "Bio–Groove Total Hip System Surgical Technique", 1986, pp. 1, 6.
Steven H. Fried, "Acetabular Cup Holder Surgical Technique," 1984, p. 2.
"The Role of Computerized Tomography Scan in Preoperative Evaluation of the Adult Dislocated Hip", Dr. David G. Mendes, Clinical Orthopaedics and Related Research, Nov.-Dec. 1981, vol. 161, pp. 198-202.
"A Prototype Femoral Stem Utilizing CAT and CAD/CAM", Dr. Richard P. Gilberty et al., Orthopaedic Review, vol. XII, No. 8, Aug. 1983, pp. 59-63.
"Possibilities of Geometric XRay Examination of Pelvis for Replacing Half of the Pelvic by an Artificial Pelvis", H. Gerngross et al., Orthopadie, 118 (1980), pp. 331-336.
"Computer-Aided Manufacture of Individual Endroprostheses", G. Aldinger et al., Archives of Orthopaedic and Traumatic Surgery, vol. 102, No. 1 (1983), pp. 31-35.
Richards Medical Company: SPECTRON ™ System Conversion Femoral Endoprosthesis Product Brochure, Memphis, Tenn., 1983.

Primary Examiner—Randall L. Green
Assistant Examiner—Stephanie Iantorno
Attorney, Agent, or Firm—Flehr, Hohbach, Test, Albritton & Herbert

[57] ABSTRACT

Preoperative planning method for systematically performing a total hip replacement utilizing CT scan data to size acetabular and femoral components, orient the actabular cup, and equalize leg lengths. The method includes one or more of the steps of selecting acetabular cup size according to dimensions revealed by a certain acetabular CT slice, determining stem size of the femoral component according the scanned dimensions of the medullary canal, reaming the acetabulum and orienting the face of the acetabular cup placed therein according to a reference plane defined by three CT-defined reference points on the acetabulum, equalizing leg lengths by performing the femoral neck osteotomy according the preselected component dimensions and bone/cartilage removal. The invention envisions the use of CT and NMR devices to achieve bony contour definitions.

6 Claims, 8 Drawing Sheets

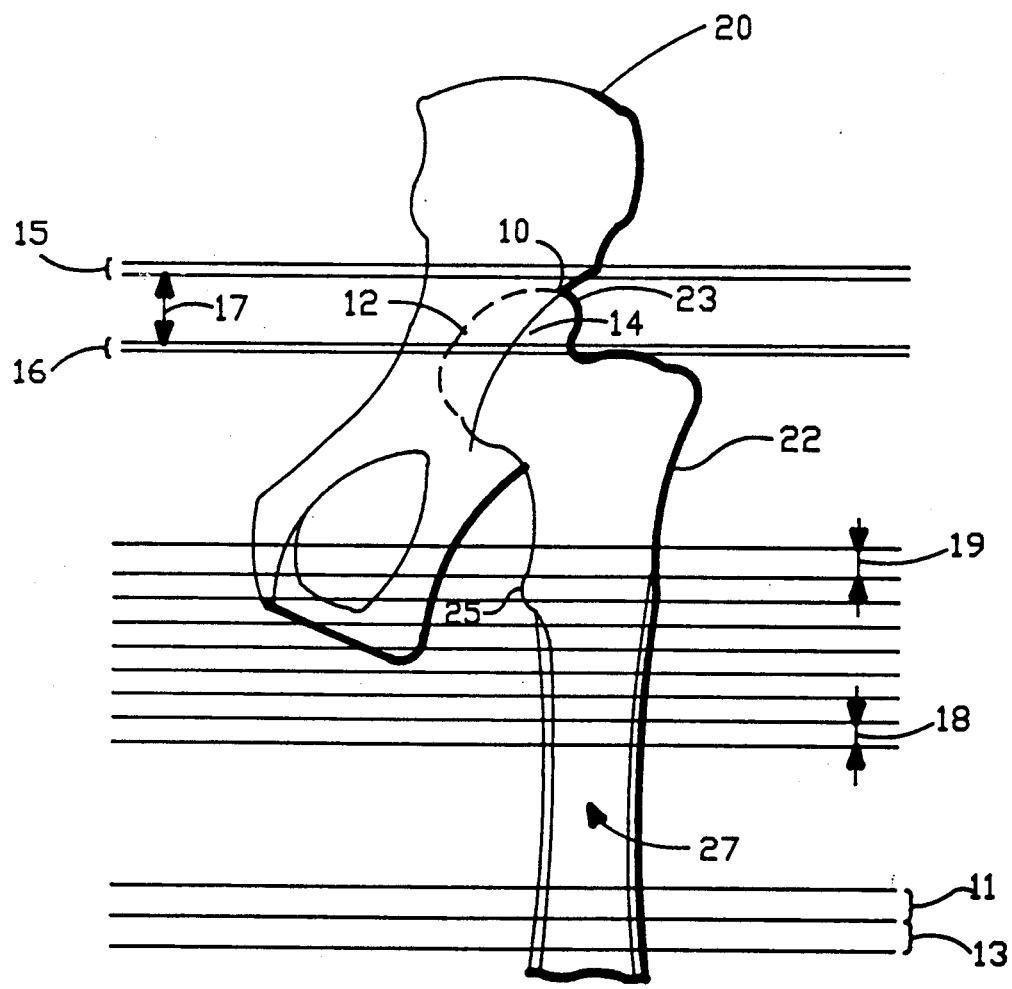
FIG.—1

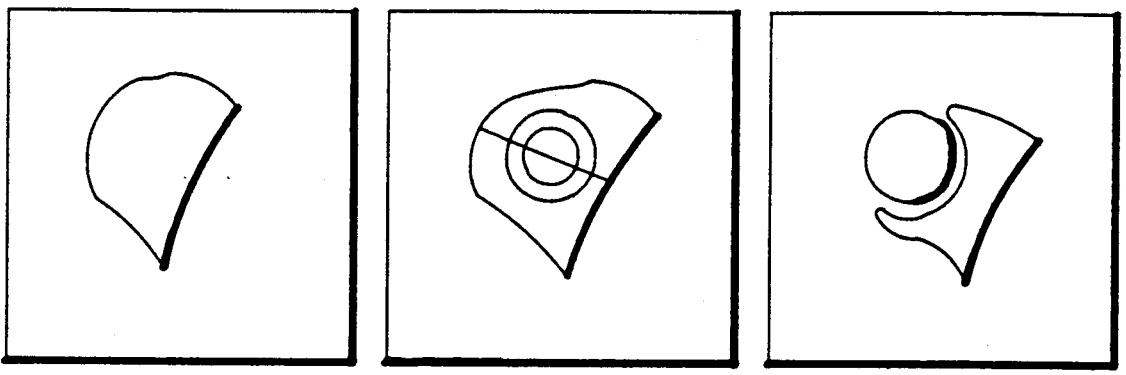
FIG.—2A   FIG.—2B   FIG.—2C
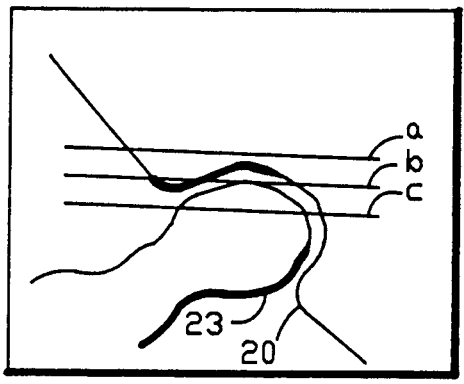
FIG.—2D
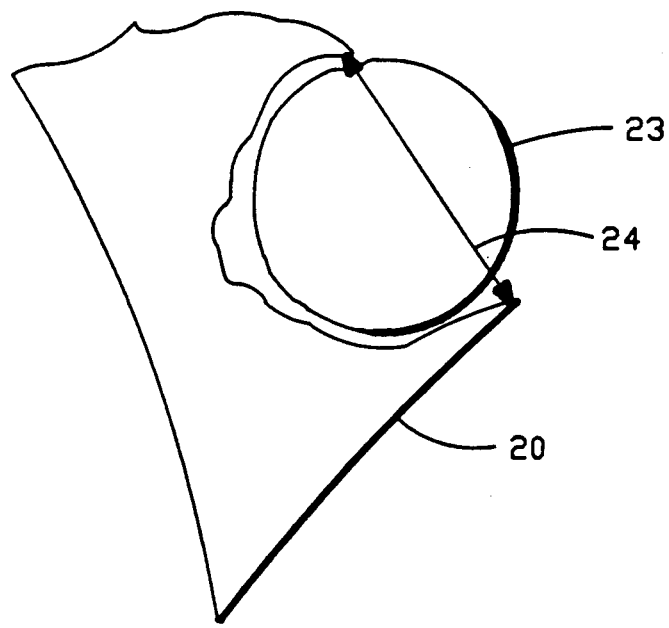
FIG.—3

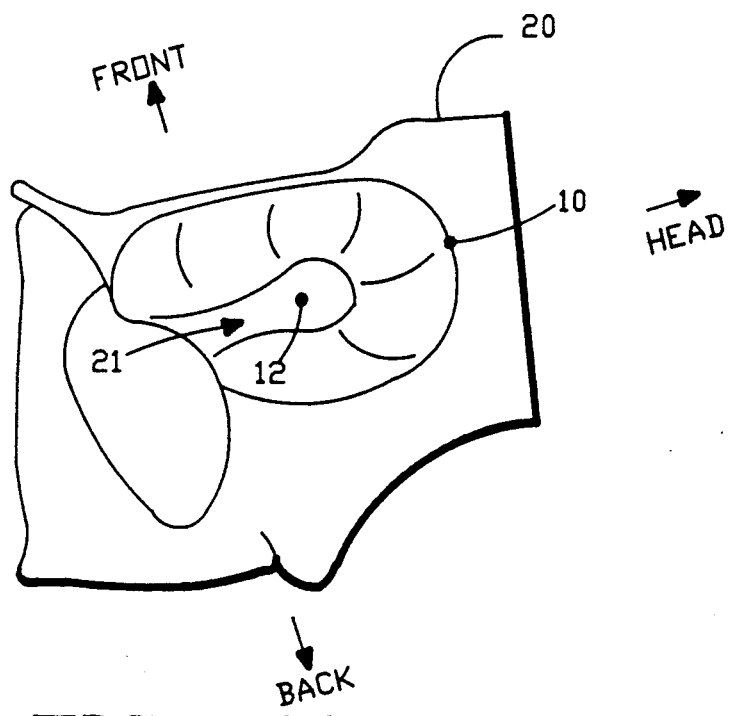
FIG.–4A
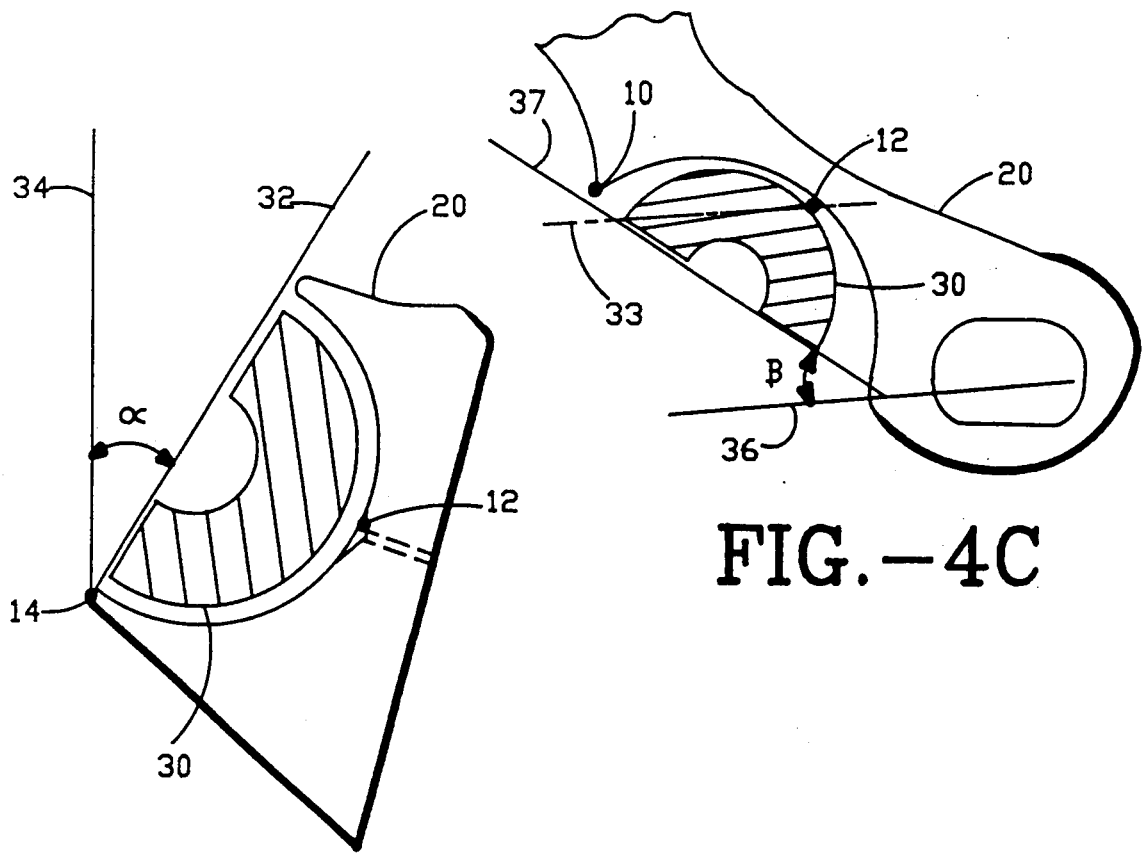
FIG.–4C
FIG.–4B

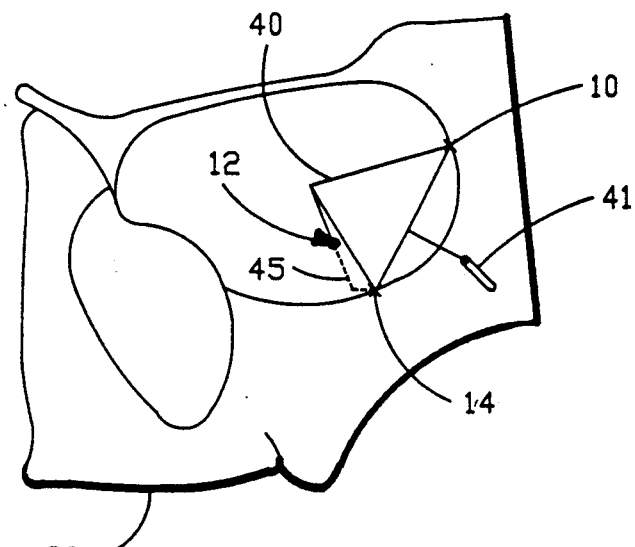
FIG.-5A
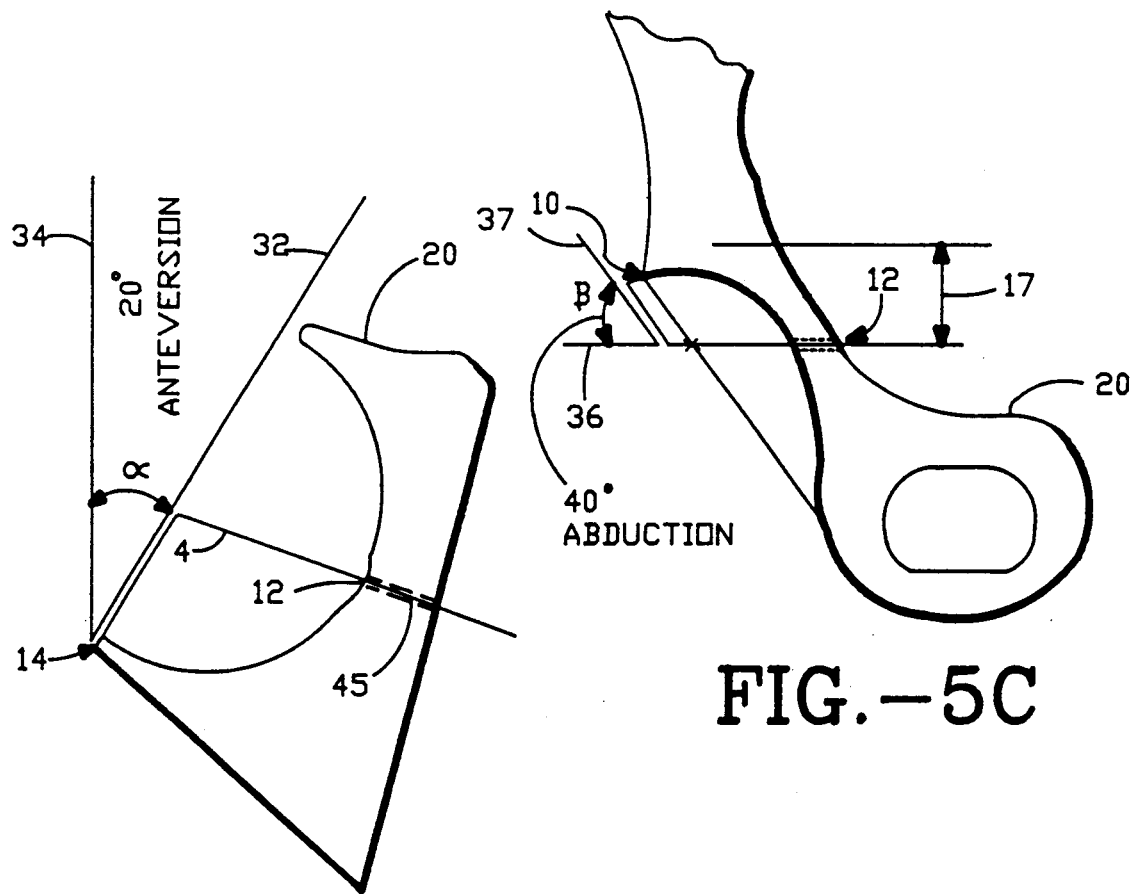
FIG.-5B
FIG.-5C

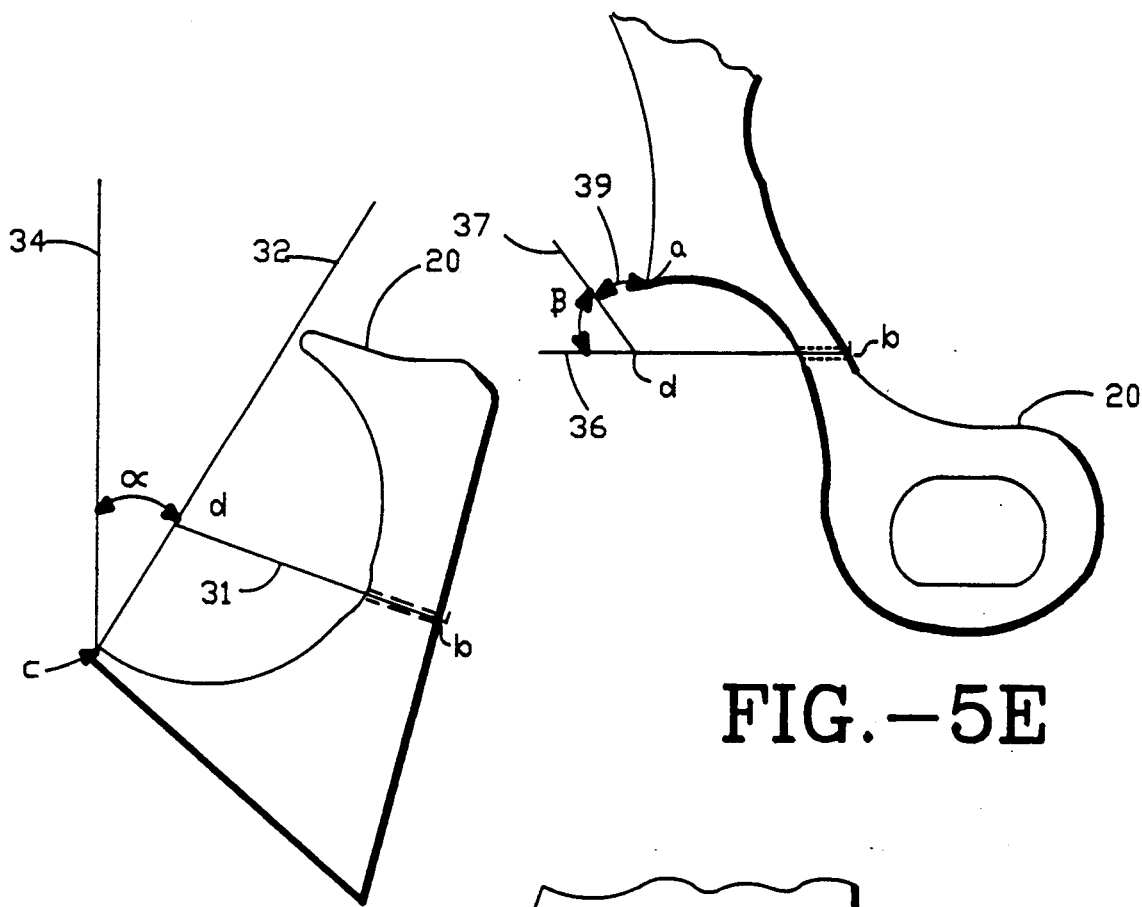
FIG.–5D
FIG.–5E
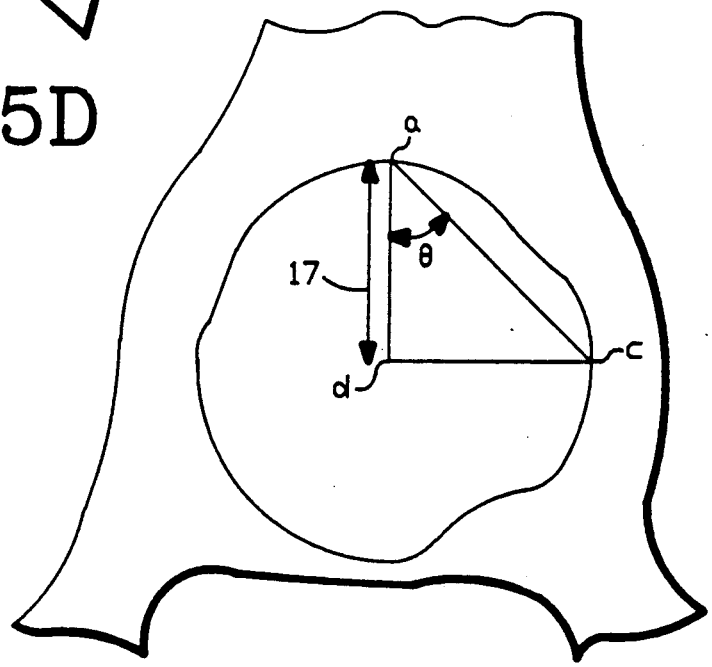
FIG.–5F

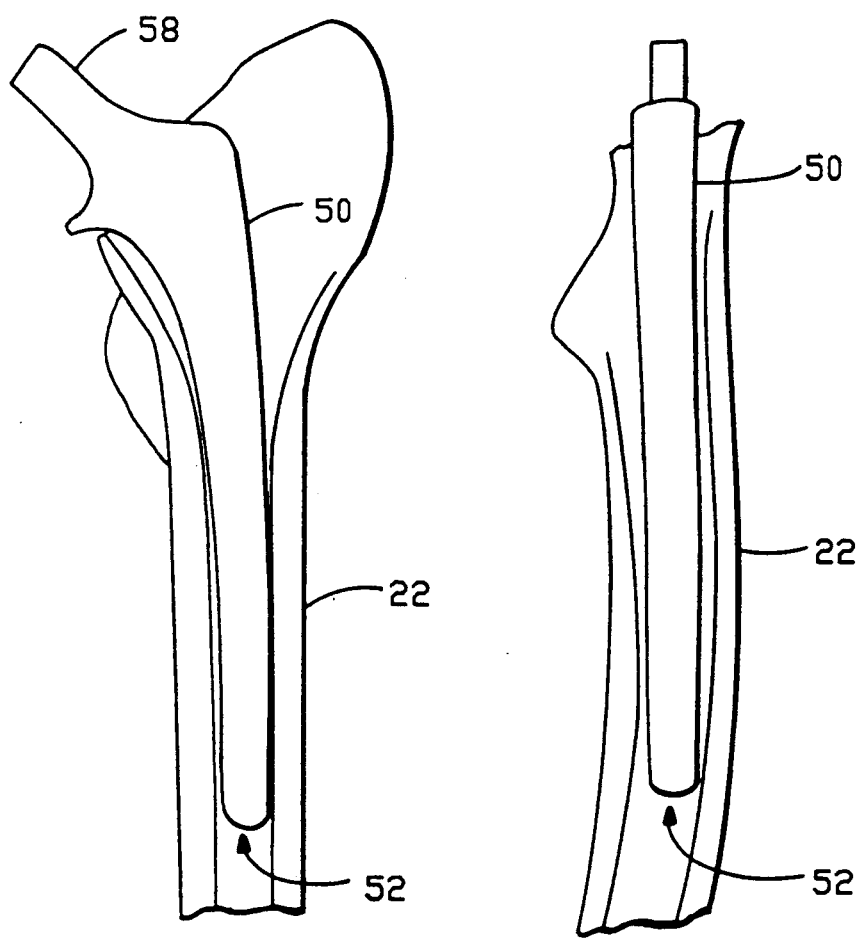
FIG.—7A   FIG.—7B

SURGICAL METHOD FOR HIP JOINT REPLACEMENT

BACKGROUND OF THE INVENTION

This invention concerns surgical procedures, but more specifically, systematic procedures using computer generated tomographic data to implant a hip prosthesis in a patient. Systematic procedures assure accuracy and consistency in orienting and sizing components of the hip prothesis to attain anatomically correct functioning results.

Surgical procedures involving total hip replacements (THR) began in 1959 and have since dramatically evolved. Initially, extraordinarily excellent results of cemented THR in the short term caused surgeons to believe that deterioration over time would not occur. Recent long term follow-up studies, however, have caused alarm by reporting aseptic loosening rates of 11-29% on the acetabular side and 29-40% on the femoral side after ten years. New cementing techniques in the 1980's including pressurization and plugging of the femoral canal, as well as improved prosthetic design, have increased the life of the hip implant. Customized sizing of femoral components also showed an improvement over the cemented THR. More recently, an entirely different technique known as bone ingrowth fixation has shown promising results, but long-term studies are yet to be made.

Nowadays, about 40% of hip replacements are being done without the use of bone cement at all. However, the success of these new implants requires that two criteria be met during implantation. They include establishing intimate contact of a porous implant surface with viable bone, e.g., that bone which can "grow" into the porous implant surface; and an initial rigid fixation of the prosthesis within the bone. Upon meeting these criteria, bone ingrowth normally occurs and early results are good.

Meeting these criteria is more difficult than using cement to provide fixation. Success entails careful preoperative planning and precise preparation of the bone at surgery. An infinite number of anatomical variations of the femoral canal exists whereas only a limited number of prosthesis sizes are available. In most instances, bone must be machined to accept a 18 standard size and shape of prosthesis. The task requires an experienced surgeon to obtain predictably good results, but as a 20 matter of fact, the majority of hip replacements are performed by orthopaedic surgeons who do not specialize in joint replacement surgery and thus may have limited expertise in this area.

Preoperative planning of bone ingrowth (and also cemented) THR is key to successful implantation. Nearly all available hip systems emphasize planning in their surgical technique manuals. These manuals give considerable attention to details of using acetate x-ray templates to plan the procedures. However, standard preoperative planning using plain x-rays and overlay templates is subject to many errors due to the magnification distortion of x-ray films and the difficulty in obtaining right-angle radiographic views of the hip joint. Most planar x-ray templates are enlarged about 20% relative to the actual patient's anatomy which represents an average magnification factor assuming a 40" distance between the x-ray beam source and the x-ray film table. This variable alone can interject 5-10% or 1-2 mm. error in the correct size of the femoral component and a 2-3 mm. error in the size of the acetabular component.

Most surgical THR protocols call for determination of femoral canal size during reaming or broaching of the femoral canal. This is a good method of determining a tight fit, if the reamer or rasps are always sharpened to the same degree. However, if the surgeon decides to use the next larger stem size because the reamer just used does not appear to be large enough, he must then determine whether the next larger stem fits into the femur prior to proceeding. It is critical to determine the fit preoperatively to avoid potential femoral fractures during surgery or potential leg length discrepancies by a failure to insert the prosthesis to the desired depth because it is too large. This problem is compounded by the fact that most orthopaedic surgeons do not do an adequate job of preoperative planning with templates. Furthermore, templating and is somewhat time-consuming.

It is also difficult to attain acetabular component (sometimes called a "cup") orientation and equalization of leg lengths during a THR operation. Proper cup placement depends on a knowledge of the exact position of the patient's pelvis on the operating room table and a system of visually estimating the position of the component orientation guide instrument. Both of these factors are subject to considerable error making this part of the procedure one of the most difficult and requiring considerable judgment and experience. At present, there are no known methods for systematically determining cup orientation relative to the patient's pelvis.

Leg length equalization both depends on the preoperative planning and on intraoperative measurement. Preoperative planning by the overlay templates only provides a rough estimate of leg length equalization. Intraoperative leg length measurement is usually done by subjective and inaccurate tests such as "shuck" and assessment of abductor muscle tension. At least one prior study substantiated leg-length differentials as much as 1.5 cm in approximately 20% of patients following unilateral THR. This is a distressing fact, since leg length inequality is quite obviously apparent to the patient immediately after surgery.

Prior solutions addressing some of the aforementioned problems include the work of Dr. David G. Mendes published in an article titled "The Role of Computerized Tomography Scan in Preoperative Evaluation of the Adult Dislocated Hip" which appeared in the November-December 1981 issue of Clinical Orthopeadics and Related Research, Vol. No. 161. At page 201 thereof, he discusses the use of three-dimensional CT data to help determine the choice of placement of the socket and to help determine component sizes. A German publication by Gerngro β, et al. titled "Möglichkeiten geometrischer Röntgenuntersuchung des Beckens für den halbseitigen Beckenersatz" appearing at page 331-336 of Zeitschrift für Orthopädie, Vol. 118, describes the use of CT data to reconstruct a hemipelvis with which a femur is to function. Drs. Richard P. Giliberty, et al., in a publication titled "A Prototype Femoral Stem Utilizing CAT and CAD/CAM" appearing in the periodical Orthopaedic Review, Vol. XII, No. 8, describe the geometical aspects of designing a femoral stem in connection with a THR process using CT data, and specifically discusses factors to be considered for achieving a desired angle of femoral neck inclinations in the frontal and transverse (anteversion)

planes, as well as the design of the femoral stem in a fashion to minimize stress points in the intramedullary canal. Still relating to femoral stem design, Messrs. Aldinger, Fisher and Kurtz also describe a CT design process in their publication titled "Computer-aided Manufacture of Individual Endoprostheses" appearing in the Archives of Orthopeadic and Tramatic Surgery, Vol. 102, No. 1.

In view of the foregoing, it is an objective of the present invention to remove some of the "guess work" and poor judgment often occurring in a THR surgical procedure.

It is a further objective of the present invention to attain greater accuracy in sizing and orientation of prosthetic components utilizing computer tomographic data, such as CT scans, NMR scans and PET (positron emission transmissions) data.

It is a more specific objective of the present invention to establish systematic procedures for defining a reference plane about the patient's pelvis (or acetabulum) by which an acetabular socket can be correctly oriented in order to implant an anatomically correct hip system.

It is a further objective of the present invention to provide a method for properly selecting the optimum size and dimensions of femoral and acetabular components of a hip prosthesis.

It is yet another objective of the present invention to provide mathematical means for leg-length equalization based upon dimensions of the hip components and certain fixation points defined within the patient's acetabulum.

It is a further objective of the present invention to utilize computer tomographic data, in conjunction with certain defined surgical procedures, to accurately implant a hip prosthesis.

SUMMARY OF THE INVENTION

In accordance with a primary aspect of the present invention, a method of replacing a hip joint in a patient comprises the steps of developing bony contour representations of the patient's acetabular region by techniques such as computer tomography, defining fixation points about the acetabular region on the basis of the bony contour representations, determining an acetabular reference angle relative to the fixation points, reaming subchondral bone from the acetabulum at an angle relative to the acetabular reference angle thereby to form a properly oriented socket for placement of an implantable acetabular component therein, fixing the acetabular component in said reamed socket of the acetabulum, and arranging together the femoral and acetabular components thereby to form the hip prothesis.

Computer topographic techniques include radiant energy CT scans, NMR tomography, PET tomography and the like which usually take the form of several scan slices of the patient's anatomy to produce two- or three-dimensional coordinate representations. Fixation points define a plane by which the acetabular cup and femoral component can be oriented and/or aligned relative to the coronal and abduction planes. Three or more points define the reference plane.

In a further aspect of the invention, leg-length equalization is attained by mathematically determining the level of femoral neck osteotomy in accordance with a reference point defined relative to the implanted femoral and acetabular components and/or by measuring the amount of bone and cartilage removed during implantation of the acetabular component.

Other aspects, objectives and advantages of the invention will become readily apparent upon review of the succeeding description taken in connection with the accompanying drawings. The invention though is pointed out with particularity by the appended claims.

BRIEF DESCRIPTION OF THE DRAWINGS

FIG. 1 depicts a typical pelvis region of a patient illustrating planar slices of a preferred CT scan protocol for obtaining contour data of the patients acetabulum and proximal femur.

FIGS. 2A–2C depict planar images of successive CT slices about a preferred fixation point, e.g., the superior rim of the acetabulum, useful for defining a reference plane (or angle) for reaming a socket and orienting the acetabular component in the hemipelvis.

FIG. 2D depicts planes a, b, and c corresponding to views of FIGS. 2A–2C.

FIG. 3 is a planar image of the central region of the acetabulum useful for sizing the acetabular component of the hip prosthesis.

FIGS. 4A–4C illustrate placement of an acetabular cup relative to anteversion and abduction angles which are defined relative to preferred fixation points about the acetabulum.

FIGS. 5A–5F illustrate positioning of a reaming guide useful for aligning a drill guide during reaming of the acetabulum to form the socket in which the acetabular component is implanted.

FIGS. 7A and 7B are anterior/posterior and lateral views respectively of a patient's femur including a femoral stem of the implanted hip prosthesis.

DETAILED DESCRIPTION OF THE INVENTION

Figure 6:
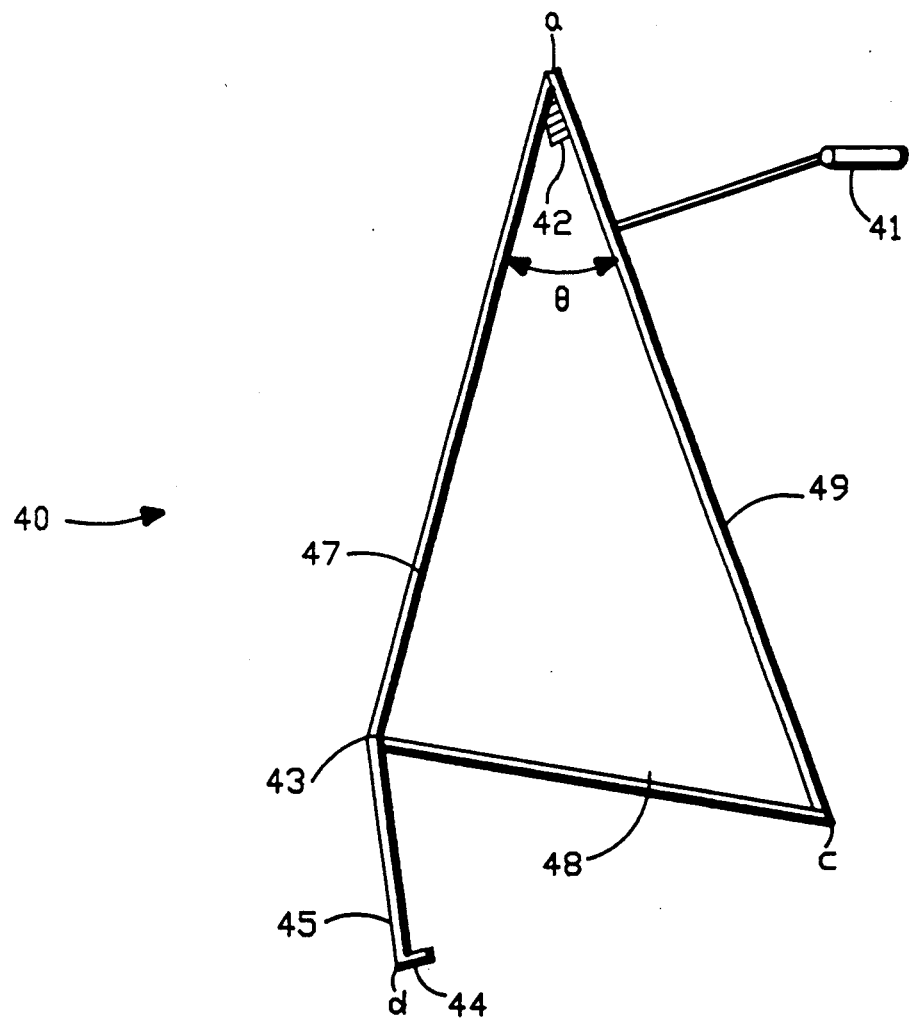
FIG. 6 shows a preferred reaming or orientation jig for guiding the reaming device.

In practicing the invention, I obtain CT scans of a patient's pelvis region, as indicated according to a CT scan protocol of FIG. 1, to define bony contours of the acetabulum and proximal end of the femur. NMR and PET techniques may also be employed to define such bony contours. Image processing using computer-generated data enables accurate determination of component sizing, cup orientation and leg-length equalization. Based upon the initial scan data, the operating surgeon predetermines the type of prosthesis, femoral component head size and neck length, any preoperative leg-length discrepancy, and the desired orientation of the acetabular component in terms of abduction in the coronal plane and anteversion the transaxial plane.

FIG. 1 illustrates the hemipelvis region 20 which includes an acetabular 12 and femur 22. The femoral head 23 articulates with the acetabulum. In a preferred scanning process, I use a commercially available CT scanner, such as a GE-9800 to obtain thick and thin slices of the patient's hemipelvis region, and a CEMAX-1500 image processor manufactured by Cemax, Inc. of Santa Clara, Calif. to analyze the CT data. The patient's leg is stabilized to prevent movement during the scanning procedure. The orientation jig is used for reaming the socket for positioning the acetabular cup, as later discussed.

A preferred fixation point 10 is the superior rim of the acetabulum, e.g., its 12 o'clock position. From point 10, two other fixation points 12 and 14 are uniquely selected thereby defining a reference plane from which anteversion and abduction angles are measured. Advantageously, fixation point 10 at the superior rim can be easily located at the time of surgery to correlate it visually with the scan data. In this fashion, planning can be confirmed at the time of surgery.

During the scan protocol, the CT technician scans the acetabulum from a cephalad to caudal direction beginning at its upper extent using 4 or 5 mm. thick slices until locating the most superior aspect of the acetabular rim. Once located, the region of superior rim is scanned with several thin slices near the slice 15 in order to find the precise location of the 12 o'clock position of the superior rim. Thin slices are 1.5 or 2.0 millimeters thick.

FIGS. 2A–2C show several thin slices near the superior rim. FIG. 2A shows a slice slightly above the superior rim while FIG. 2C shows a slice slightly below the superior rim. FIG. 2B shows the slice 15 located precisely at the superior rim just above the proximal end 23 (FIG. 1) of the femur 22. FIG. 2D depicts planes a, b and c corresponding to views of FIGS. 2A–2C.

After identifying the location of the first fixation point 10 at the superior rim, the operator makes another thin acetabular slice 16 preferably two centimeters distal to the plane of the superior rim 10, as indicated by space 17, or alternatively near the center of the femur's proximal end 23. Slice 16 extends approximately through the center of the acetabulum and is used to locate the two other bony landmarks, e.g., fixation points 12 and 14, for orientation and sizing of the acetabular component.

The femur 22 (FIG. 1) is scanned with contiguous thick slices of about one-centimeter from a starting slice 19 approximately one centimeter proximal of the lesser trochanter 25 to a slice 18 about eight centimeters distal thereof. If the patient is to receive a prosthesis intended to fit tightly within the isthmus of the femoral medullary canal 27, two additional one-centimeter thick slices 11 and 13 are made thirteen to fifteen centimeters distal to the initial femoral scan 19.

I determine the size of the acetabular component by measuring the length of chord 24 of the central acetabular CT slice 16 extending though the femoral head 23, the planar view of which is depicted in FIG. 3. I select the outer diameter of the acetabular cup to be approximately two to three millimeters larger than chord 24 to account for reaming of subchondral bone from the acetabulum during preparation of the socket.

Referring to FIGS. 4A–4C, I next define in three axes the set of spatial coordinates of three fixation points 10, 12 and 14 providing bony landmarks according to the CT images of the acetabulum. FIG. 4A is a perspective view of the acetabulum exposing the acetabular fossa 21. FIG. 4B depicts a slice of the acetabulum in the transaxial plane and FIG. 4C depicts a slice of the acetabulum in the coronal plane. Angle $\alpha$ in FIG. 4B defines the anteversion angle of plane 32 in the transaxial plane 34 Plane 32 parallels the face of the implanted acetabular cup 30. Angle $\beta$ of FIG. 4C, on the other hand, defines the abduction angle of plane 37 in the coronal plane 36. Planes 32 and 37 are the same, but are designated differently for sake of clarity in explanation.

Fixation point 10 marks the superior rim of the acetabulum, fixation point 12 marks the inner wall of the acetabulum exactly two centimeters distal to the point 10, and fixation point 14 marks the posterior rim to the acetabulum at the same level as point 12. Fixation point 12 resides in a plane 33 that is spaced two centimeters distal to superior rim 10. Plane 33 parallels coronal plane 36. As subsequently explained in greater detail, fixation points 10, 12 and 14 provide a reference for orienting an orientation jig parallel to the face of the acetabular cup to be implanted in the acetabulum. The orientation jig contains adjustable legs and spacers which sit upon the fixation points so as to provide a reference plane parallel to the plane 32 (or 37) of the face of cup 30. In this way, one is assured of attaining correctly and systematically the proper anteversion and abduction angles after surgery.

It is apparent, however, that these initial fixation points ca also be established at other locations about the hemipelvis rather than being restricted to the acetabulum. The objective is to define some sort of reference angle or reference plane for making consistent measurements preoperatively and intraoperatively, particularly with reference to establishing desired anteversion and abduction angles, as well as, leg length equalization.

FIGS. 5A–5F illustrate placement of a triangular orientation jig 40 used for reaming the acetabular socket. The triangular jig 40 has three feet at its respective apices which rest upon bony landmarks 10, 12 and 14. It also has coupled thereto a drill guide for placement of a guide pin in the pelvis to orient the acetubular reaming operation. When the socket is reamed accordingly, the acetabular cup will set properly to attain correct anteversion and abduction angles.

FIG. 6 is a preferred jig 40, but it may obviously vary in construction according the definition of bony landmarks and other factors. The jig 40 preferably comprises a triangular device having three legs 47, 48 and 49. Leg 47 is about two centimeters and the angle $\Theta$ between legs 47 and 49 is adjustable according to patient parameters. Further, joint 43 between legs 47 and 48 includes and adjustable-length arm 45 to accommodate varying wall thickness of the acetabulum. To brace the jig 40 in the acetabulum socket (see FIG. 5B), a hole is drilled through the rear of the acetabulum at fixation point 12. Arm 45 extends through this hole as seen in FIGS. 5A and 5B. Jig 40 also includes three feet 42, 44 and 46. Feet 42 and 46 include adjustable spacers (FIG. 6) to permit establishing the proper reference plane.

Relative to defined fixation points 10–12, I geometrically determine the distances to a plane 32 of the face of cup 30 while in the ideal position. In the ideal position, cup 30 preferably is oriented to attain 40° abduction in the coronal plane and 20° anteversion in the transaxial plane.

Using the calculated distances for the spacers and adjustable arm of the jig 40, I attain the correct reference. I refer to FIGS. 5D–5F in explaining my calculations. Also, note that points a and c correspond with fixation points 10 and 14, respectively. Point b is juxtaposed the acetabular wall of fixation point 12. From a transaxial image through points b and c (x,y coordinates), I determine an anteversion angle $\alpha$ of 20° (FIG. 5D) with the apex at point c. Next, I determine the distance 31 along a perpendicular line extending from point b to point d on line 32 rotated by angle from line 34 in the transaxial plane. This distance determines the length of arm 45 (FIG. 6) of the jig 40.

To determine the offset to be provided by the spacers at point a, I determine an abduction angle $\beta$ (FIG. 5E) of 40° from line 36 in the coronal plane with its apex at the previously determined point d. I then measure the distance 39 from the abduction line 37 to point a located at, the superior rim. Distance 39 represents the offset to be provided by the spacers at foot 42 (FIG. 6) of the jig 40. No spacers are needed at junction 46 at point c of the jig 40.

To find the appropriate angle Θ (FIG. 5F), I merely measure the angle between triangular legs a-d and a-c in the sagittal plane. The distance a-c is determined geometrically from known angle Θ, right angle adc, and the length of leg a-d being equal to two centimeters.

Thus, the triangular jig may now be set according to the known angle Θ, angle adc being equal to 90°, leg a-d being two centimeters, leg a-c being measured as describe above, distance b-c being calculated as described above, and spacers at foot 42 at point a being calculated as described above. When the jig 40 is set accordingly, its triangular base provides a reference plane establishing 20° anteversion and 40° abduction, as planned. Further, the outrigger drill guide attached thereto provides a reference angle that is perpendicular to the reference plane. Using the reference plane and reference angle, the acetabular socket may be correctly aligned when reamed, and the acetabular component (e.g., cup) is properly oriented in a systematic fashion.

In the actual surgery, point 10 at the superior acetabular rim as well as the posterior acetabular rim are cleared of all capsule and labrum as is normally done. A 7/64" drill hole is made through the central wall of the acetabulum exactly 2 centimeters distal to point 10 by means of a drill guide (not shown). The triangular orientation jig 40, prepared and adjusted as described above, is positioned on the face of the acetabulum 20 with its three preadjusted feet 42, 44 and 46 placed respectively on the three bony landmarks 10, 12 and 14 previously defined.

The drill guide outrigger 41 attached to triangular guide 40 allows placement of a reference guide wire into the posterior wall of the acetabulum (outside of the socket). This guide wire provides a visual reference for correct axial positioning of the acetabular component. When the component is aligned, it is press-fitted for bone ingrowth, or cemented in place by conventional techniques.

As shown in FIGS. 7A and 7B, the size of the femoral component 50 is determined from a 3-dimensional CT image of the medullary canal 52 of the femur 22. The 3D image of the medullary canal 52 can be rotated through 360° to compare its size with templates of the femoral component to assure the closest fit.

Figures 8A, 8B:
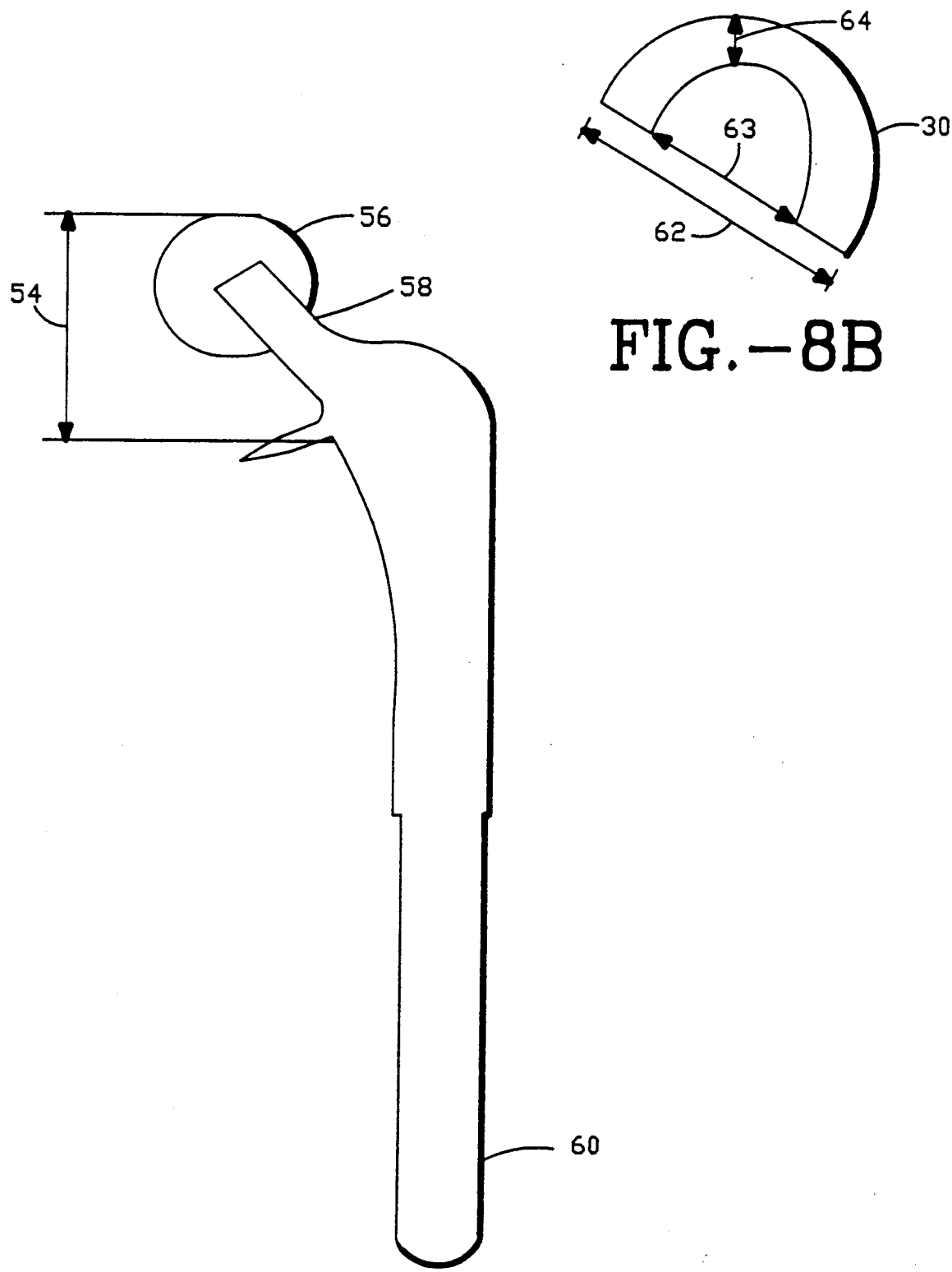
FIGS. 8A and 8B show respective components of a hip prosthesis described in connection with leg-length equalization procedures.

Once the acetabular and femoral component sizes are known, I perform leg length equalization and determine the location of the femoral neck osteotomy. Equalization and osteotomy is realized from the concept that once the size of the implanted components are known, then the appropriate amount of bone can be resected (the femoral head and neck) to equalize the leg lengths. Referring to FIG. 8A and 8B, the cross-sectional thickness of the acetabular component 30 is known upon determining the size, e.g., outer diameter, of the acetabular cup. The height 54 of the femoral head 56 and neck section 58 (with or without a collar) is known upon determination of the size of stem 60 and selection of the size of the femoral component head 56 according to constraints determined after examining the medullary canal. The other required variables to determine leg length are the amount of bone and/or cartilage removed from the superior aspect of the acetabulum, the amount of femur to be removed and any preoperative leg length discrepancy to be corrected.

The amount of acetabular cartilage and bone removed is found by placing a 1/8" drill hole into the superior dome of the acetabulum to a specified depth, e.g., 5 mm., prior to reaming. A flexible drill with a 5 mm. stop is used to make this reference hole. Once the socket has been reamed, the hole is sounded and its new depth can be measured with a calibrated gauge.

Following the determination of the acetabular and femoral component sizes, a rough estimate of the level of the 20 femoral neck cut is made so as to minimize modification of the osteotomy. For example, if a patient has a one-centimeter deficiency on the side to be operated, and a 52 mm. cup and a femoral prosthesis with a 32 mm. head size and a medium neck length is desired, then I systematically make the following computations:

Vertical Dimension of Prosthesis

Cup thickness = $\frac{52 - 32 \text{ mm}}{2}$ = 10 mm.

Femoral component length (med. neck, 32 mm. head) (dimensions known from manufacturer)  = 50 mm.

Total = 60 mm.

Bone/Cartilage Removed
Acetabular side = 3 mm.
Femoral side = X (unknown)

Total = X + 3 mm.
Dimensions of Prostheses added = Bone/Cartilage removed
60 mm. = X + 3 mm.
57 mm. = X = Femoral head and neck to be removed The 10 millimeters leg length discrepancy is equalized by removing 10 millimeters less bone, e.g., 47 millimeters, or by using a long neck femoral prosthesis having a vertical height of 55 millimeters and removing 5 millimeters less bone, e.g., 52 millimeters. Since the femoral neck osteotomy must be made prior to preparation of the acetabulum, it may be required to make a revision of the osteomotomy after reaming the socket. The neck should be cut shorter than anticipated and recut after preparing the socket, if necessary. The femoral neck osteotomy is made from the reference point of the superior aspect of the femoral head and not from the more difficult landmark of the lesser trochanter as is traditional. A special caliper was designed to measure the distance from the top of the head to the level of the neck resection.

The above process sets forth the preferred sequences for performing a total hip replacement using coordinate data derived from CT scans or like devices. In some instances, it may be necessary to replace only one of the hip components in which case the process is modified to account for a partial hip implant process to account for the preexisting component or anatomy. Further, the sequences may be varied in order depending upon circumstances known to the skilled surgeon and/or circumstances of the patient. Thus, the teachings herein are not limited to the processes shown or described, but include all such revisions and/or changes embraced by the appended claims and derived from the teachings provided by the above description.

What is desired to be protected by U.S. Letters Patent follows:

1. A method of implanting a hip prosthesis in a patient having at least a portion of an acetabulum and a femur, the prosthesis including an acetabular component for attachment to a femoral component to provide predetermined anteversion and abduction angles, said method comprising the steps of:

A. selecting the size of said femoral and acetabular components;
  B. defining a reference plane relative to said acetabulum by identifying the location of fixation points about the acetabulum according to at least one of CT scan data, PET data and NMR data, a first one of said fixation points being located at the superior rim of said acetabulum, a second of said fixation points being located on the inner wall of said acetabulum at a fixed distance distal to said first fixation point wherein said second fixation point is located at the posterior rim of said acetabulum, and a third one of said fixation points being located on the rim of said acetabulum at a fixed distance distal to said first fixation point thereby to define said reference plane for establishing an orientation for implanting said acetabular component;
  C. positioning about the acetabulum a reference guide having predetermined anteversion and abduction angles relative to said reference plane;
  D. reaming subchondral bone using an appropriate reaming device of said acetabulum relative to said guide thereby to form a properly oriented socket for placement of the acetabular component;
  E. positioning a drill guide at first, second and third fixation points which are triangularly related to one another to establish said reference plane for said acetabular component;
  F. drilling a hole through the central wall of the acetabulum at an angle relative to said reference plane;
  G. placing a visual reference marker in said drilled hole;
  H. visually aligning said reaming device with said reference guide during said reaming step thereby to obtain accurately the proper orientation of said acetabular component after implant thereof; and
  I. fixing said acetabular component in said reamed socket of said acetabulum thereby to establish the predetermined anteversion and abduction angles when functioning with said femoral component.

2. A method as recited in claim 1 further comprising positioning said reference guide relative to said at least three fixation points thereby to accurately orient said reaming device during said reaming step.

3. A method as recited in claim 1 wherein said femoral component includes a stem for placement inside the medullary canal of said femur, said method further comprising the step of:
  determining the dimensions of the stem of said femoral component according to radiant energy scans of said medullary canal obtained in said defining step.

4. A method as recited in claim 1 wherein said acetabular and femoral components have predetermined dimensions further comprising the step of:
  determining the location of a femoral neck osteotomy of the femur according to radiant energy scans obtained in said defining step in order to equalize the length of legs of said patient.

5. A method as recited in claim 4 wherein the femoral component includes a femoral head portion wherein a reference point for establishing said femoral neck osteotomy is the superior aspect of the femoral head portion of the femoral component in relation to said acetabular component.

6. A method as recited in claim 4 or 5 wherein the amount of bone and cartilage removed from the superior aspect of the acetabulum is used as a factor in determining femoral resectioning to establish leg equalization, and said amount is determined by drilling a hole of a predetermined depth in the superior dome of the acetabulum prior to said reaming step and measuring the hole depth after said reaming step thereby to gauge the amount of bone and cartilage removed.

* * * * *